(12) United States Patent
Boshra et al.

(10) Patent No.: US 10,398,370 B2
(45) Date of Patent: Sep. 3, 2019

(54) WEARABLE ELECTRONIC DEVICE INCLUDING WRIST BIOMETRIC SENSOR FOR ACQUIRING SKIN TEXTURE PATTERN IMAGES AND RELATED METHODS

(71) Applicant: Apple Inc., Cupertino, CA (US)

(72) Inventors: Michael Boshra, San Jose, CA (US); Dale R. Setlak, Merritt Island, FL (US)

(73) Assignee: APPLE INC., Cupertino, CA (US)

( * ) Notice: Subject to any disclaimer, the term of this patent is extended or adjusted under 35 U.S.C. 154(b) by 0 days.

(21) Appl. No.: 15/987,577

(22) Filed: May 23, 2018

(65) Prior Publication Data
US 2019/0000370 A1    Jan. 3, 2019

Related U.S. Application Data

(60) Provisional application No. 62/527,558, filed on Jun. 30, 2017.

(51) Int. Cl.
*A61B 5/00* (2006.01)
*A61B 5/117* (2016.01)
*G06F 21/32* (2013.01)

(52) U.S. Cl.
CPC ............ *A61B 5/442* (2013.01); *A61B 5/0064* (2013.01); *A61B 5/0086* (2013.01); *A61B 5/117* (2013.01); *A61B 5/448* (2013.01); *A61B 5/681* (2013.01); *A61B 5/6824* (2013.01); *G06F 21/32* (2013.01); *A61B 2562/0271* (2013.01)

(58) Field of Classification Search
CPC .................................. G06F 21/32; A44C 5/18
USPC ........................................................ 340/5.82
See application file for complete search history.

(56) References Cited

U.S. PATENT DOCUMENTS

| | | | |
|---|---|---|---|
| 7,599,530 B2 | 10/2009 | Boshra | |
| 9,304,624 B2 | 4/2016 | Fadell et al. | |
| 2014/0196131 A1* | 7/2014 | Lee | G06F 21/35 726/7 |
| 2015/0304322 A1* | 10/2015 | Zaidi | G06K 9/00892 382/115 |
| 2016/0267338 A1* | 9/2016 | Rice | A61B 5/0059 |
| 2016/0283808 A1* | 9/2016 | Oganezov | G06K 9/00885 |
| 2016/0314290 A1* | 10/2016 | Baca | G06K 9/00885 |
| 2016/0354042 A1 | 12/2016 | Shim et al. | |

(Continued)

OTHER PUBLICATIONS

Blasco et al., "A Survey of Wearable Biometric Recognition Systems," Journal ACM Computing Surveys (CSUR), vol. 49 Issue 3, Dec. 2016, Article No. 43, pp. 1-34.

*Primary Examiner* — Fabricio R Murillo Garcia
(74) *Attorney, Agent, or Firm* — Allen, Dyer, Doppelt, + Gilchrist, P.A.

(57) ABSTRACT

A wearable electronic device may include a device body and a device band coupled to the device body for securing the device to a wrist of a user. The wearable electronic device may also include a wrist biometric sensor carried by one of the device body and the device band. The wrist biometric sensor may include biometric sensing pixels. The wearable electronic device may also include a processor coupled to the wrist biometric sensor and configured to cooperate with the biometric sensing pixels to acquire skin texture pattern images from adjacent portions of the user's wrist, and perform at least one authentication function based upon the skin texture pattern images.

11 Claims, 8 Drawing Sheets

(56) References Cited

U.S. PATENT DOCUMENTS

2016/0373438 A1 12/2016 Yoon
2017/0109931 A1* 4/2017 Knorr .................. G06T 19/006

* cited by examiner

WEARABLE ELECTRONIC DEVICE INCLUDING WRIST BIOMETRIC SENSOR FOR ACQUIRING SKIN TEXTURE PATTERN IMAGES AND RELATED METHODS

RELATED APPLICATIONS

The present application claims the priority benefit of provisional application Ser. No. 62/527,558 filed on Jun. 30, 2017, the entire contents of which are herein incorporated in its entirety by reference.

TECHNICAL FIELD

The present invention relates to the field of electronics, and, more particularly, to the field of wearable electronic devices including a wrist biometric sensor.

BACKGROUND

Biometric sensing and matching is a reliable and widely used technique for personal identification or verification. In particular, a common approach to biometric identification involves scanning a sample fingerprint or an image thereof and storing the image and/or unique characteristics of the fingerprint image. The characteristics of a sample fingerprint may be compared to information for reference fingerprints already in a database to determine proper identification of a person, such as for verification purposes.

A biometric sensor may be particularly advantageous for verification and/or authentication in an electronic device, and more particularly, a portable device, for example. Such a biometric sensor may be carried by the body of a portable electronic device, for example, and may be sized to sense a biometric, for example, a fingerprint from a single-finger. Where a biometric sensor is integrated into an electronic device or host device, for example, as noted above, it may be desirable to perform authentication, particularly while performing another task or an application on the electronic device.

SUMMARY

A wearable electronic device may include a device body and a device band coupled to the device body for securing the device to a wrist of a user. The wearable electronic device may also include a wrist biometric sensor carried by one of the device body and the device band. The wrist biometric sensor may include a plurality of biometric sensing pixels. The wearable electronic device may also include a processor coupled to the wrist biometric sensor and configured to cooperate with the plurality of biometric sensing pixels to acquire skin texture pattern images from adjacent portions of the user's wrist, and perform at least one authentication function based upon the skin texture pattern images.

The wrist biometric sensor may include an infrared (IR) thermal image sensor, for example. Skin texture may have a first thermal pattern associated therewith and hair may have a second thermal pattern associated therewith. The processor may be configured to perform the authentication function by thermally distinguishing the first and second thermal patterns, for example. The IR thermal image sensor may include a microbolometer, for example.

The wrist biometric sensor may include an electric field sensor. The wrist biometric sensor may include an optical image sensor, for example.

The wrist biometric sensor may be carried by the device body. The wrist biometric sensor may be carried by the device band.

The wearable electronic device may also include a display carried by the device body and coupled to the processor. The processor may be configured to display a current time on the display, for example. The wearable electronic device may also include wireless communications circuitry coupled to the processor and configured to perform at least one wireless communications function.

A method aspect is directed to a method of performing at least one authentication function. The method may include using a processor of a wearable electronic device that includes a device body, a device band coupled to the device body for securing the device to a wrist of a user, a wrist biometric sensor carried by one of the device body and the device band, coupled to the processor and that includes a plurality of biometric sensing pixels. The processor may be used to cooperate with the wrist biometric sensor to acquire skin texture pattern images from adjacent portions of the user's wrist, and perform at least one authentication function based upon the skin texture pattern images.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to refer to like elements in different embodiments.

Figure 1:
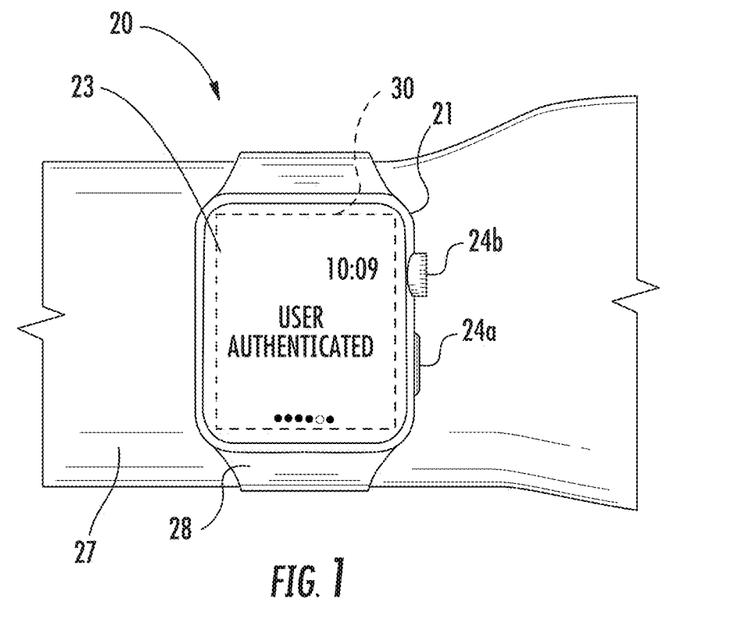
FIG. 1 is a top view of a wearable electronic device being worn by a user according to an embodiment.
Figure 2:
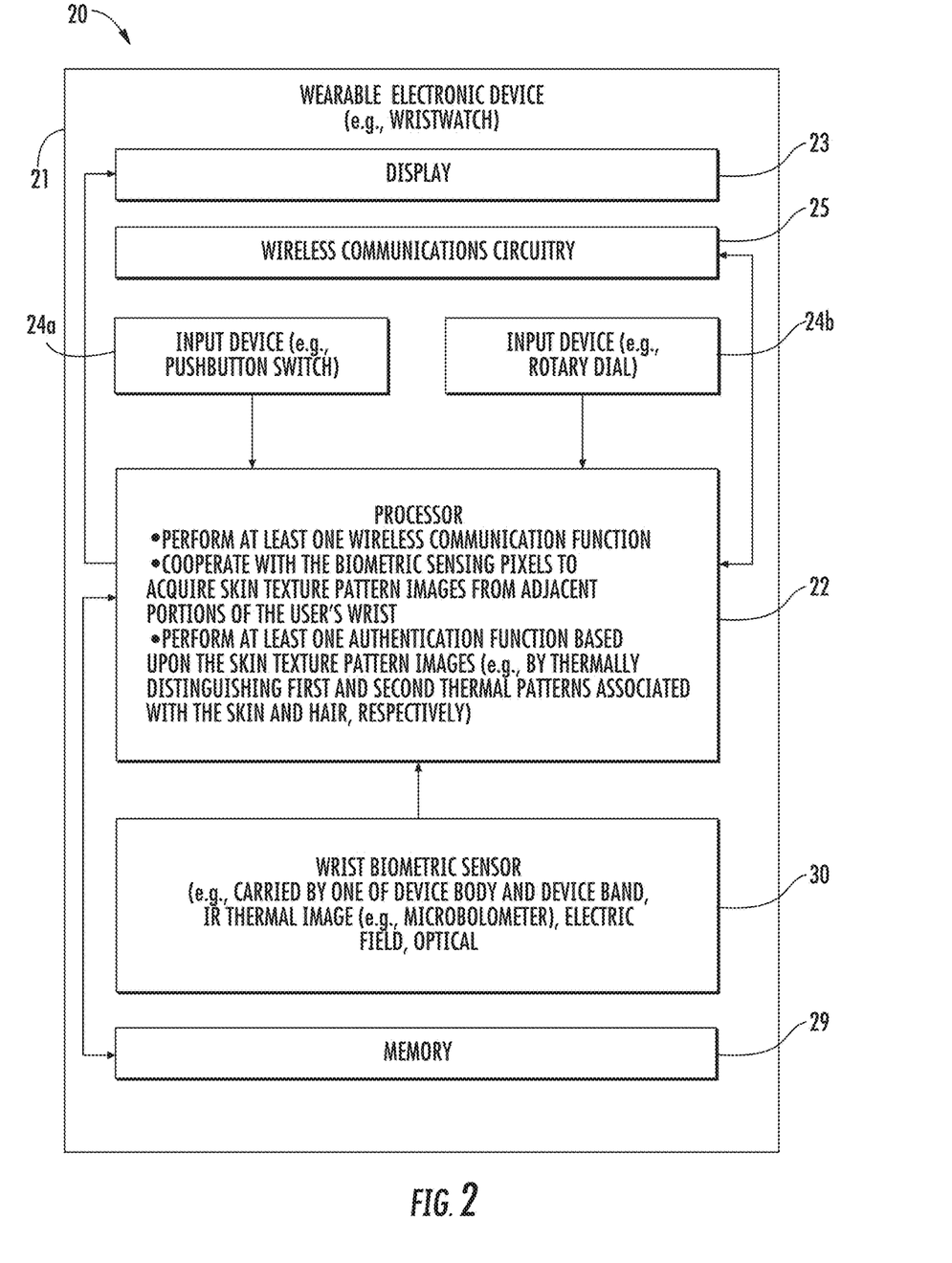
FIG. 2 is a schematic block diagram of the electronic device of FIG. 1.
Figure 3:
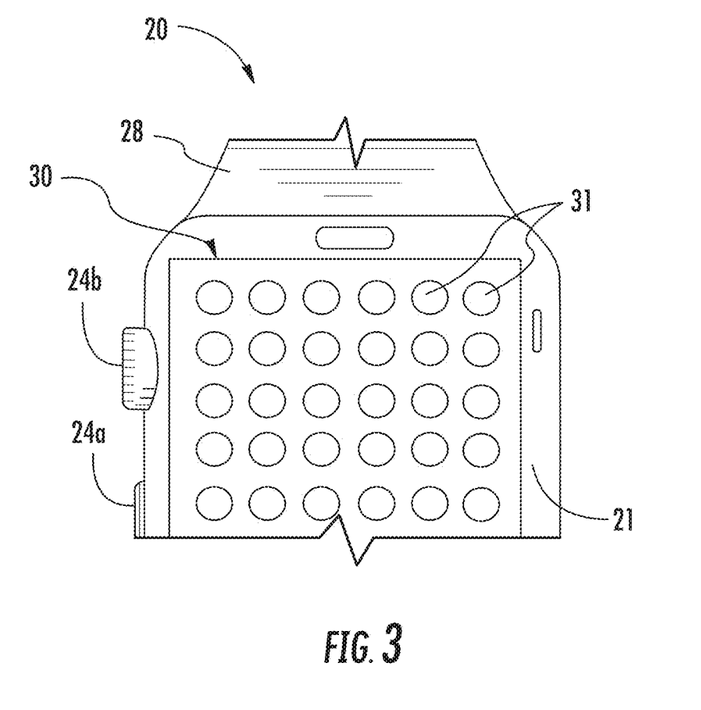
FIG. 3 is a bottom view of a portion of the electronic device of FIG. 1.

Referring initially to FIGS. 1-3, a wearable electronic device 20 illustratively includes a device body 21 and a processor 22 carried by the device body. The electronic device 20 is illustratively a mobile wireless communications device, for example, a wearable wireless communications device, and includes a device band 28 or strap for securing it to a wrist 27 of a user. The wearable electronic device 20 may be another type of wearable electronic device, as will be appreciated by those skilled in the art.

Wireless communications circuitry 25 (e.g. cellular, WLAN Bluetooth, etc.) is also carried within the device body 21 and coupled to the processor 22. The wireless communications circuitry 25 cooperates with the processor 22 to perform at least one wireless communications function, for example, for voice and/or data. In some embodiments, the wearable electronic device 20 may not include wireless communications circuitry 25.

A display 23 is also carried by the device body 21 and is coupled to the processor 22. The display 23 may be a liquid crystal display (LCD), for example, or may be another type of display, as will be appreciated by those skilled in the art. The wearable electronic device 20 may function as a wristwatch, for example, such that the processor 22 cooperates with the display 23 to display a current time. The processor 22 may cooperate with the display 23 to display other types of information, for example, application or communications notifications, movement based data, biometric data, etc.

Finger-operated user input devices 24a, 24b, illustratively in the form of a pushbutton switch and a rotary dial are also carried by the device body 21 and are coupled to the processor 22. The pushbutton switch 24a and the rotary dial 24b cooperate with the processor 22 to perform a device function in response to operation thereof. For example, a device function may include a powering on or off of the wearable electronic device 20, initiating communication via the wireless communications circuitry 25, and/or performing a menu function.

The wearable electronic device 20 illustratively includes a wrist biometric sensor 30 carried by the device body 21. The wrist biometric sensor 30 may be carried by the device body 21 such that it makes contact with the skin on the dorsal side of the user's wrist 27. The wrist biometric sensor 30 may be sized to be about the size of the backside or dorsal side of the device body 21 (i.e., extending to adjacent a periphery or sidewall of the device body).

The wrist biometric sensor 30 may be an infrared (IR) thermal image based sensor and include biometric sensing pixels 31 each operating, for example, at a wavelength of 1-5 microns. For reference, near infrared sensing of blood vessels may occur at about 800 microns. More particularly, the wrist biometric sensor 30 may include a microbolometer, wherein each microbolometer defines a biometric sensing pixel 31.

The processor 22 cooperates with the wrist biometric sensing pixels 31 to acquire skin texture pattern images from adjacent portions of the user's wrist 27. The processor 22 may perform an authentication function based upon the skin texture images. For example, the processor 22 may perform image matching between the acquired skin texture pattern images and stored skin texture pattern images stored in a memory 29 coupled to the processor during an enrollment process. Based upon successful matching, the processor 22 may enable one or more device functions or unlock the wearable electronic device 20, for example. Other and/or additional functions may be enabled or disabled based upon performing the authentication function. Additionally, the processor 22 and the wrist biometric sensor 30 may cooperate to perform continuous "background" authentication, for example, at set intervals, while the wearable electronic device 20 is being worn by the user (i.e., the device body 21 is adjacent the user's wrist 27).

Further details of the acquisition of the skin texture pattern images using the wrist biometric sensor 30 will now be described. As will be appreciated by those skilled in the art, the user's wrist 27, both the dorsal (top) and palmar (bottom) have a skin texture associated therewith. Thus, skin texture is usable as a biometric identifier.

As noted above, the wrist biometric sensor 30 is carried by the device body 21 to be in contact with the dorsal side of the user's wrist 27. However, many users have a relatively large amount of hair on the dorsal side of their wrist, for example, with respect to palmer side. The hair on the dorsal side of the user's wrist 27 is about the same size as the texture features of interest, for example, skin or texture cracks. Thus, hair can obfuscate any sensed or acquired texture pattern and it may be desirable for effects of this hair to be reduced for improved accuracy skin texture pattern matching.

Figure 4:
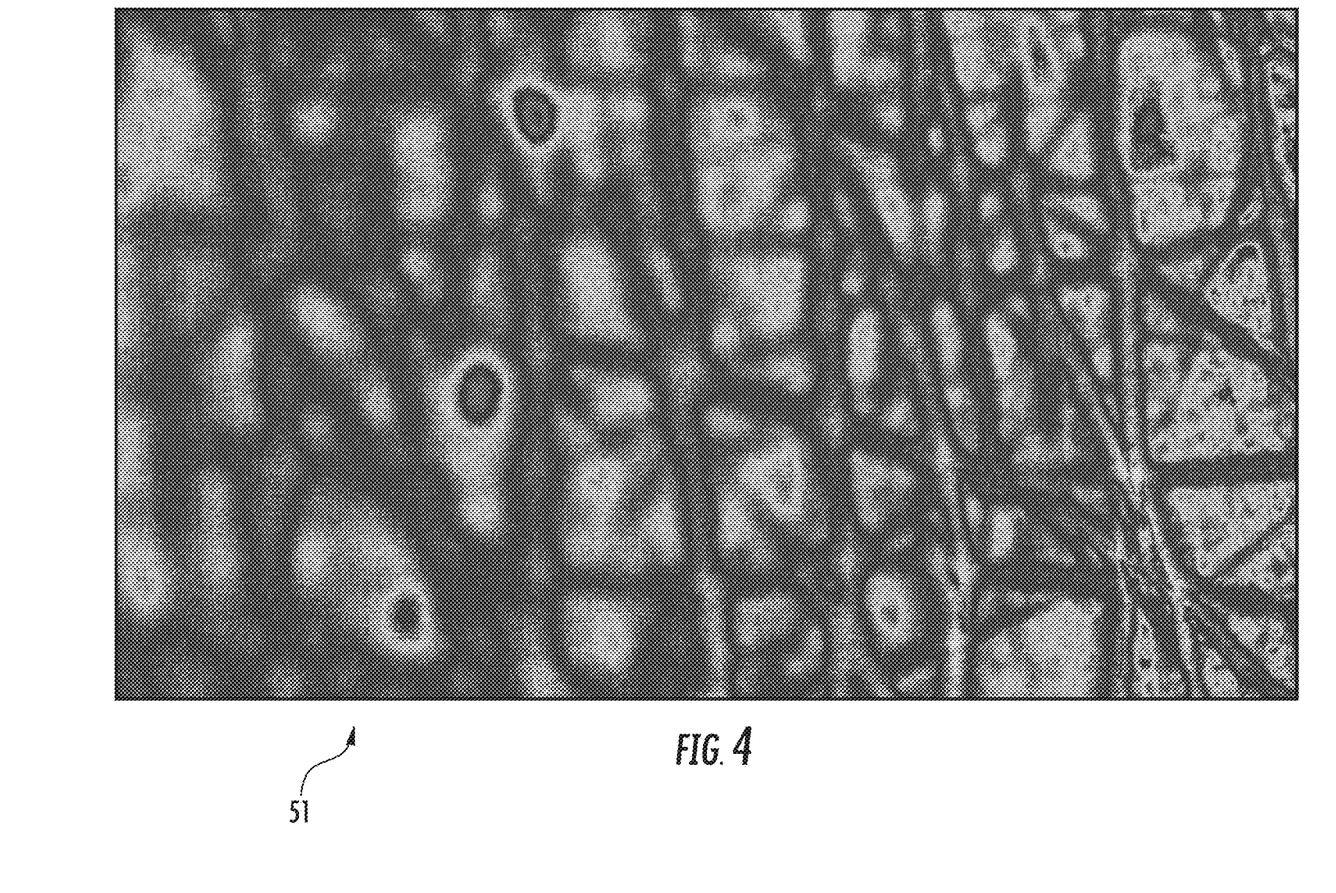
FIG. 4 is a skin texture pattern image of a user's wrist using an infrared (IR) based wrist biometric sensor according to an embodiment.

The wrist biometric sensor 30 has an IR thermal image sensor, and may provide improved accuracy skin texture pattern acquisition through hair. This is because skin texture has a first thermal pattern associated therewith, and hair has a second thermal pattern associated therewith. More particularly, skin texture cracks are generally warmer than the surrounding skin, and hair is cooler than the surrounding skin. By using an IR thermal image sensor as the wrist biometric sensor 30, hair can be distinguished, thermally, from skin texture cracks by temperature. Additionally, by using an IR thermal image wrist biometric sensor 30, no illumination may be desirable. Image 51 in FIG. 4 is an exemplary IR thermal image of a user's wrist, palmer side.

Skin textures generally do not have fiducials that are clearly visible to humans for matching as compared to fingerprints, for example. However, the processor 22 and wrist biometric sensor 30 may not rely on humanly discernable fiducials for matching. Accordingly, similar to electric field sensing techniques, the processor may extract textural elements and represent them in an abstract orientation vector field for use in matching, for example, using ridge-flow mappings, vectors, etc.

Figure 5:
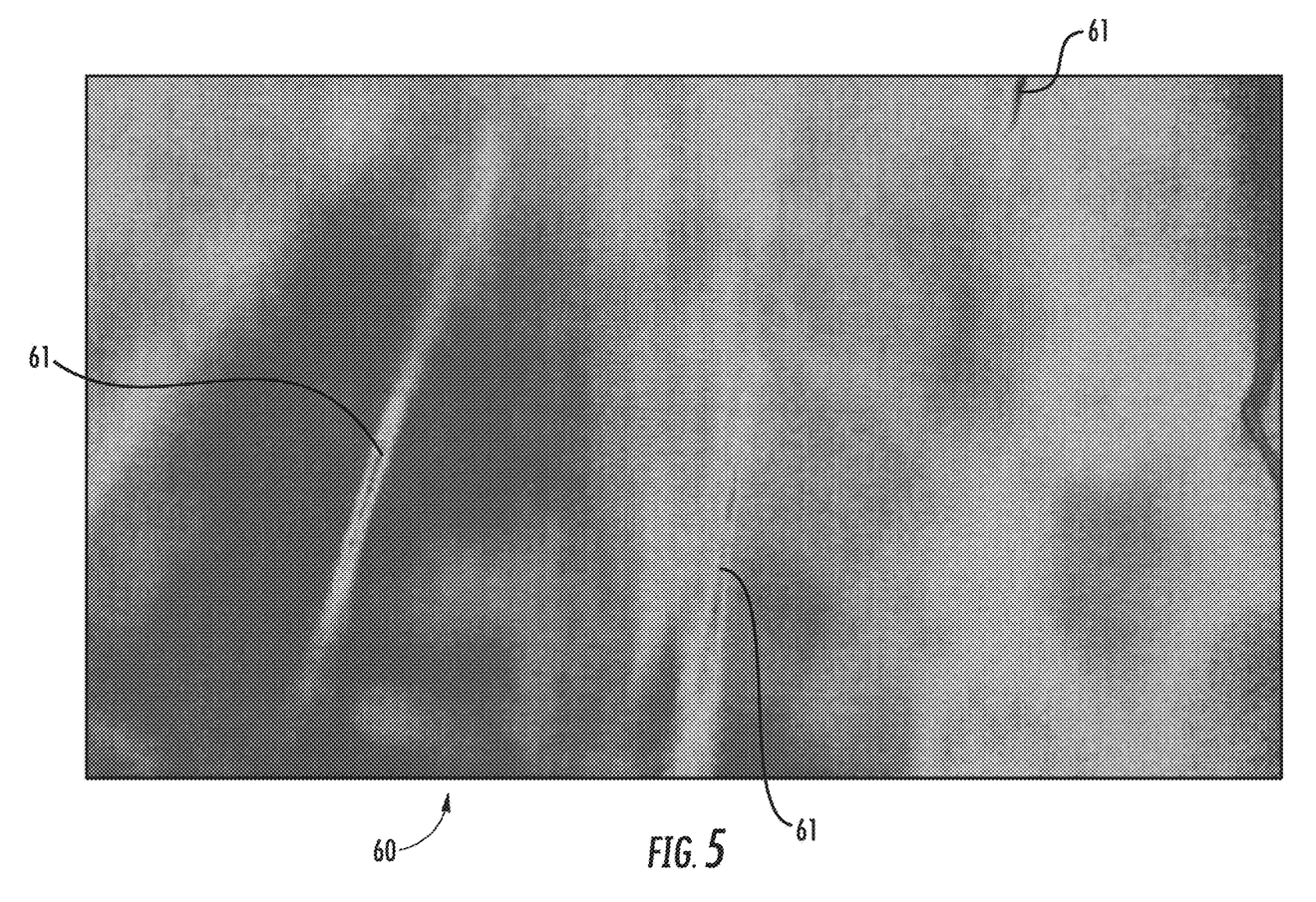
FIG. 5 is another skin texture pattern image of a user's wrist using an IR based wrist biometric sensor according to an embodiment.

Referring now to FIG. 5, the image 60 is a mid-wave infrared imager (MWIR) camera image of a user's left wrist, dorsal side. Illustratively, several hairs 61 appear to be visible in this image as cooler linear objects.

Figure 6:
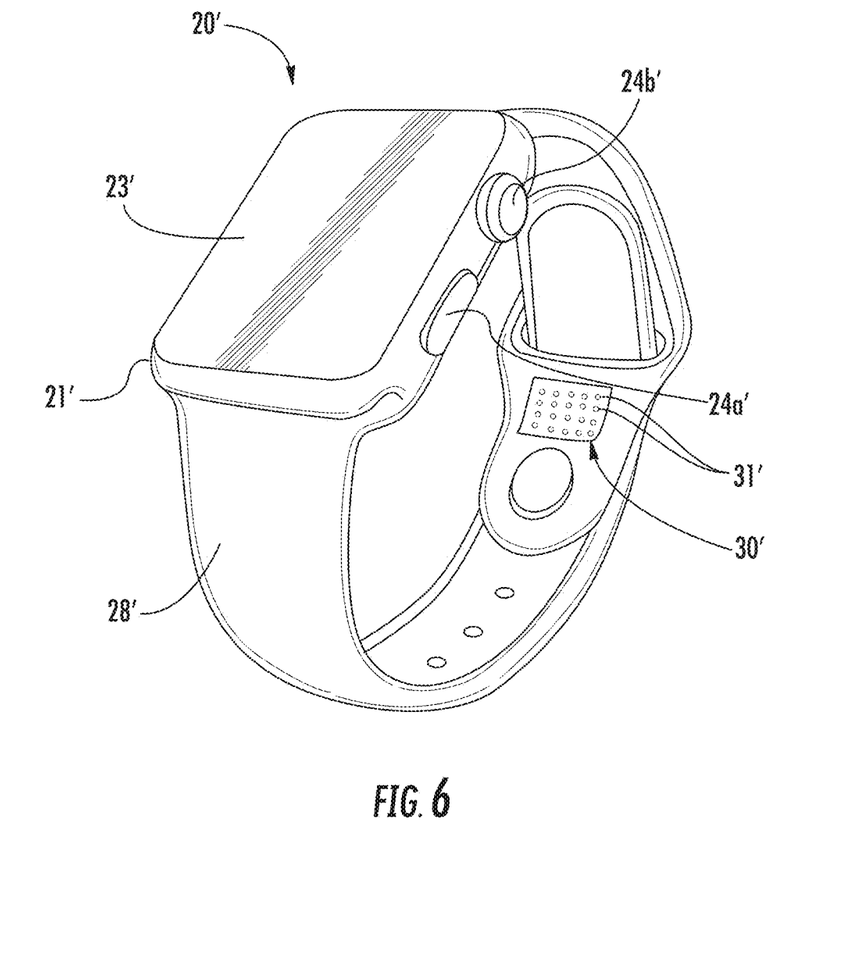
FIG. 6 is a perspective view of a wearable electronic device according to another embodiment.

Referring now to FIG. 6, in another embodiment, the wrist biometric sensor 30' may be carried by the device band 28' adjacent the palmer side of the user's wrist. Where the wrist biometric sensor 30' is carried adjacent the palmer side of the user's wrist, it may be desirable to use either an electric field wrist biometric sensor or an optical wrist biometric sensor having electric field sensing pixels or optical sensing pixels, respectively. Of course, an IR thermal image based wrist biometric sensor may be used.

Similar to an IR thermal image based wrist biometric sensor, illumination may not be desirable when using an electric field based wrist biometric sensor. However, in contrast to an IR thermal image based wrist biometric sensor, it may be desirable that an optical wrist biometric sensor include an illumination device.

Figure 7:
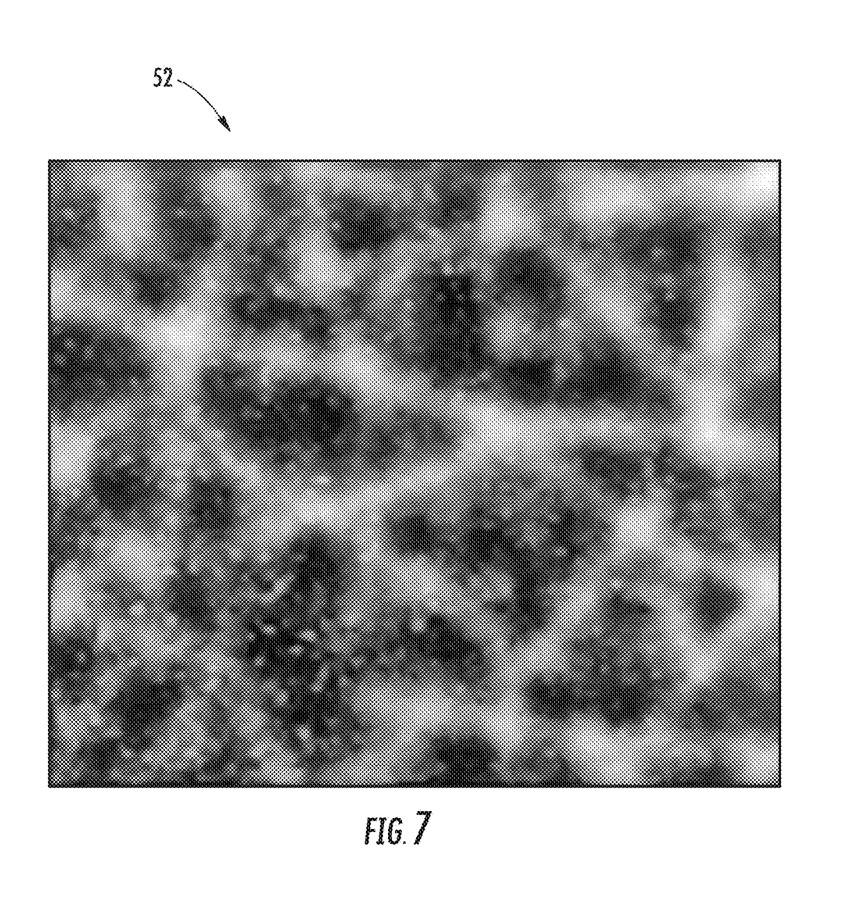
FIG. 7 is a skin texture pattern image of a user's wrist using an electric field based wrist biometric sensor according to an embodiment.

Referring now to image 52 in FIG. 7, a skin texture image of a user's wrist is illustrated using an electric field wrist biometric sensor. A wearable electronic device including an electric field based wrist biometric sensor may be less complex in terms of fabrication than either of optical and IR based wrist biometric sensors.

Figure 8:
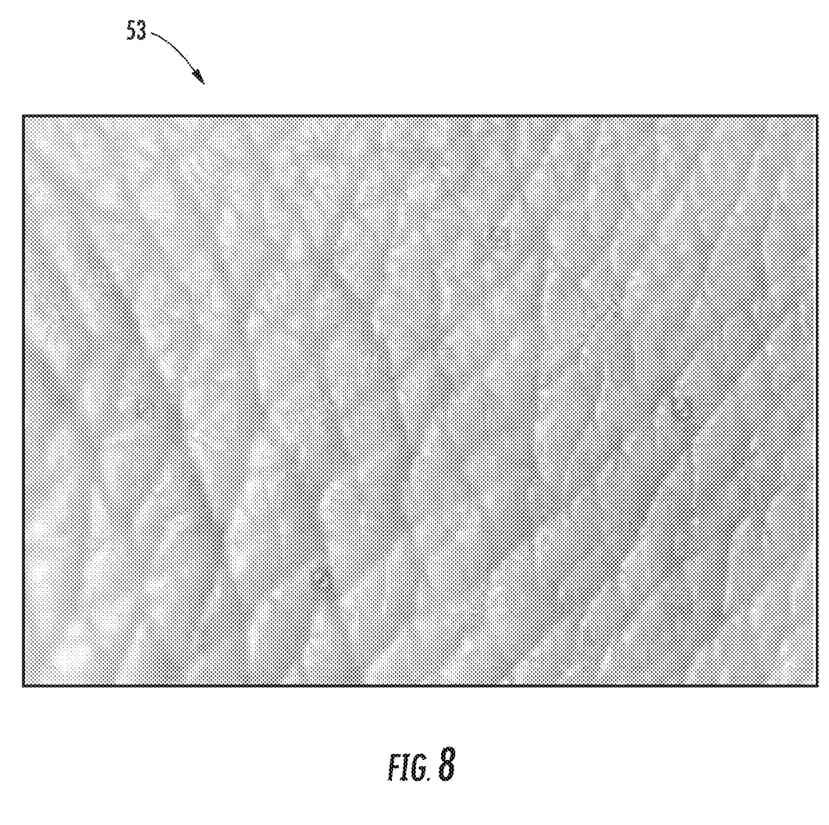
FIG. 8 is a skin texture pattern image of a user's wrist using an optical based wrist biometric sensor according to an embodiment.

Image 53 in FIG. 8 is an image of a user's wrist using an optical wrist biometric sensor. A wearable electronic device that includes an optical based wrist biometric sensor may have improved performance with respect to both IR based and electric field based wrist biometric sensors.

While several embodiments have been described herein with respect to any of thermal images, electric field, and optical based wrist biometric sensors, it should be appreciated by those skilled in the art that different pixels in the array of biometric sensing pixels may be different types and/or may operate at different wavelengths. For example, the array of biometric sensing pixels may include any one or more of optical, electric field, and/or IR thermal image sensing pixels.

A method aspect is directed to a method of performing at least one authentication function. The method includes using a processor 22 of a wearable electronic device 20 that includes a device body 21, a device band 28 coupled to device body for securing the device to a wrist 27 of a user, a wrist biometric sensor 30 carried by one of the device body and the device band, coupled to the processor and that includes biometric sensing pixels 31. The method includes using the processor 22 to cooperate with the biometric sensing pixels 31 to acquire skin texture pattern images from adjacent portions of the user's wrist 27, and perform at least one authentication function based upon the skin texture pattern images.

The present disclosure recognizes that personal information data, including biometric data, in the present technology, can be used to the benefit of users. For example, the use of biometric authentication data can be used for convenient access to device features without the use of passwords. In other examples, user biometric data is collected for providing users with feedback about their health or fitness levels. Further, other uses for personal information data, including biometric data, that benefit the user are also contemplated by the present disclosure.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure, including the use of data encryption and security methods that meets or exceeds industry or government standards. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates embodiments in which users selectively block the use of, or access to, personal information data, including biometric data, and further contemplates user restrictions on storing data in cloud-based services and/or restricting access to the same. That is, the present disclosure contemplates that hardware and/or software elements can be provided to prevent or block access to such personal information data. For example, in the case of biometric authentication methods, the present technology can be configured to allow users to optionally bypass biometric authentication steps by providing secure information such as passwords, personal identification numbers (PINS), touch gestures, or other authentication methods, alone or in combination, known to those of skill in the art. In another example, users can select to remove, disable, or restrict access to certain health-related applications collecting users' personal health or fitness data.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A wearable electronic device comprising:
 a device body;
 a device band coupled to the device body for securing the device to a wrist of a user;
 a wrist biometric sensor comprising an infrared (IR) thermal image sensor carried by one of the device body and the device band; and
 a processor coupled to the wrist biometric sensor and configured to
  cooperate with the IR thermal image sensor to acquire skin texture pattern images from adjacent portions of the user's wrist, the skin texture pattern images comprising skin texture cracks associated with a first thermal pattern, and hair associated with a second thermal pattern different than the first thermal pattern based upon a relative temperature difference, and
  perform at least one authentication function based upon the skin texture pattern images by thermally distinguishing the first and second thermal patterns.

2. The wearable electronic device of claim 1 wherein the IR thermal image sensor comprises a microbolometer.

3. The wearable electronic device of claim 1 wherein the wrist biometric sensor is carried by the device body.

4. The wearable electronic device of claim 1 wherein the wrist biometric sensor is carried by the device band.

5. The wearable electronic device of claim 1 further comprising a display carried by the device body and coupled to the processor.

6. The wearable electronic device of claim 5 wherein the processor is configured to display a current time on the display.

7. The wearable electronic device of claim 1 further comprising wireless communications circuitry coupled to the processor and configured to perform at least one wireless communications function.

8. A wearable electronic device comprising:
 a device body;
 a device band coupled to the device body for securing the device to a wrist of a user;
 a wrist biometric sensor comprising an infrared (IR) thermal image sensor carried by one of the device body and the device band;
 wireless communications circuitry carried by the device body;
 a display carried by the device body;
 a processor coupled to the wrist biometric sensor, wireless communications circuitry, and display, and configured to
  cooperate with the IR thermal image sensor to acquire skin texture pattern images from adjacent portions of the user's wrist, the skin texture pattern images comprising skin texture cracks associated with a first thermal pattern, and hair associated with a second thermal pattern different than the first thermal pattern based upon a relative temperature difference, perform at least one authentication function based upon the skin texture pattern images by thermally distinguishing the first and second thermal patterns, and cooperate with the wireless communications circuitry to perform at least one wireless communications function.

9. The wearable electronic device of claim 8 wherein the IR thermal image sensor comprises a microbolometer.

10. A method of performing at least one authentication function comprising:

using a processor of a wearable electronic device comprising a device body, a device band coupled to the device body for securing the device to a wrist of a user, a wrist biometric sensor carried by one of the device body and the device band, coupled to the processor and comprising an infrared (IR) thermal image sensor to cooperate with the thermal IR image sensor to acquire skin texture pattern images from adjacent portions of the user's wrist, the skin texture pattern images comprising skin texture cracks associated with a first thermal pattern, and hair associated with a second thermal pattern different than the first thermal pattern based upon a relative temperature difference, and perform the at least one authentication function based upon the skin texture pattern images by thermally distinguishing the first and second thermal patterns.

11. The method of claim 10 wherein the IR thermal image sensor comprises a microbolometer.

* * * * *